United States Patent [19]

Vollenberg et al.

[11] 4,430,497
[45] Feb. 7, 1984

[54] PROCESS FOR THE PREPARATION OF 2-OXA-BICYCLO [3.3.0] OCTANE DERIVATIVES AND PRODUCTS PRODUCED THEREBY

[75] Inventors: Werner P. Vollenberg; Horst R. E. Boehlke, both of Stolberg, Fed. Rep. of Germany

[73] Assignee: Gruenenthal GmbH, Stolberg, Fed. Rep. of Germany

[21] Appl. No.: 349,678

[22] Filed: Feb. 17, 1982

[30] Foreign Application Priority Data

Feb. 26, 1981 [DE] Fed. Rep. of Germany ....... 3107248

[51] Int. Cl.³ .......................................... C07D 307/935
[52] U.S. Cl. .................................. 542/429; 549/465; 549/214
[58] Field of Search ................. 549/465, 214; 542/429

[56] References Cited

U.S. PATENT DOCUMENTS 3,912,734 10/1975 Giller et al. ......................... 424/249
4,126,744 11/1978 Ayer .................................... 549/465

FOREIGN PATENT DOCUMENTS 1599280 1/1977 United Kingdom .
2012762 12/1977 United Kingdom .

OTHER PUBLICATIONS

Hurd et al., J. Amer. Chem. Soc., vol. 83, pp. 236–240 (1961).
Sato et al., J. Amer. Chem. Soc., vol. 99, pp. 5827–5828 (1977).
Muller, Methoden der Organischen Chemie (Houben-Weyl), Fourth Edition, vol. VI, Part 3, p. 289 (1965).
Saigo et al., Chemistry Letters, pp. 769–770 (1976).
Rasmussen, Synthesis, pp. 91, 107–109 (1977).
Ogawa et al., Tetrahedron Letters, No. 37, pp. 3543–3546 (1973).
Yasumoto et al., Journal of Medicinal Chemistry, vol. 21 No. 8, pp. 738–741 (1978).

*Primary Examiner*—Henry R. Jiles
*Assistant Examiner*—Bernard Dentz
*Attorney, Agent, or Firm*—Schwartz, Jeffery, Schwaab, Mack, Blumenthal & Koch

[57] ABSTRACT

The invention relates to a process for the preparation of 2-Oxabicyclo[3.3.0]octane derivatives of the general formula

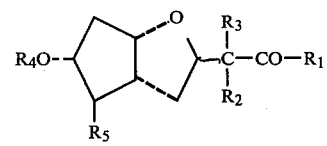

I wherein $R_1$, $R_2$, $R_3$ and $R_5$ represent organic radicals and $R_2$ and $R_3$ also may represent hydrogen and wherein $R_4$ is an acyl group or an tri-organo-silyl group and to the compounds of formula I produced by the process of the invention which compounds are valuable intermediates for the preparation of pharmacologically active compounds. The process of the invention comprises reacting a compound of the formula

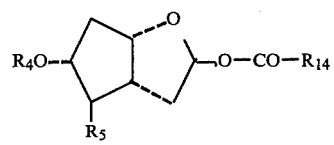

II wherein $R_{14}$ is lower alkyl or phenyl with a compound of the formula

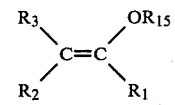

III wherein $R_{15}$ is trimethylsilyl or lower alkanoyl in an inert solvent at temperatures from about −80° C. to about +60° C. in presence of one or more Lewis acids.

14 Claims, No Drawings

PROCESS FOR THE PREPARATION OF 2-OXA-BICYCLO [3.3.0] OCTANE DERIVATIVES AND PRODUCTS PRODUCED THEREBY

The present invention relates to a process for the preparation of 2-oxa-bicyclo[3.3.0]octane derivatives and to products produced by this process. These products are valuable intermediates in the preparation of pharmacologically active compounds. The products of the process according to the invention are 2-oxa-bicyclo[3.3.0]octane derivatives corresponding to the general formula:

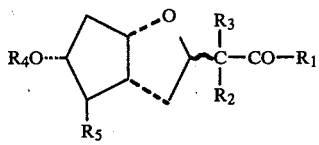

wherein
$R_1$ is an alkyl radical containing 1 to 5 carbon atoms, preferably methyl or ethyl, or represents the group

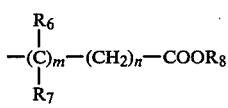

in which $R_6$ and $R_7$ may be the same or a different and represent a hydrogen atom or an alkyl radical containing 1 to 4 carbon atoms or $R_6$ and $R_7$ together represent the group $-(CH_2)_p-$ wherein p is four, five or six, and m is zero or one, n is zero, one, two or three and $R_8$ is an ester residue which easily may be split off, or
is the group $-(CH_2)_q-OR_9$, in which q is one, two or three and $R_9$ is a member of the group consisting of acetyl, benzoyl, trimethylsilyl, tert.butyldimethylsilyl and tert.butyl-diphenylsilyl, or
is an unsubstituted phenyl group or a phenyl group substituted by methyl, ethyl, trifluoromethyl or methoxy or by a group $OR_9$, in which $R_9$ has the same meaning as above, or by fluorine, chlorine or bromine or by the group

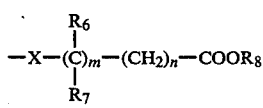

in which X is a single bond or an oxygen atom and in which $R_6$, $R_7$, $R_8$, m and n have the same meaning as above, or
represents together with the radical $R_3$ the group $-(CH_2)_r-$ in which r is three, four or five;
$R_2$ is a hydrogen atom, an alkyl radical containing 1 to 4 carbon atoms or the group $-(CH_2)_s-COOR_8$, in which $R_8$ has the same meaning as above and s is zero, one or two;
$R_3$ is a hydrogen atom, an alkyl radical containing 1 to 4 carbon atoms or is together with $R_1$ the group $-(CH_2)_r-$ defined above in the definition of $R_1$;
$R_4$ is an acyl radical which preferably is a member of the group consisting of lower alkanoyl groups containing 1 to 5 carbon atoms (especially acetyl), benzoyl and substituted benzoyl groups (especially 4-phenyl-benzoyl) or $R_4$ is tri-lower alkyl-silyl (especially trimethyl-silyl or tert.butyl-dimethylsilyl), tert.butyl-diphenylsilyl or triphenylsilyl;
$R_5$ is the group $-CH_2-OR_4'$ or the group

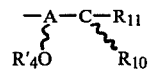

in which groups $R_4'$ within the scope of the definition of $R_4$ has the same or a different meaning as $R_4$ has and in which A represents a member of the group consisting of the groups $-CH_2-CH_2-$, (trans)$CH=CH-$ and $-C\equiv C-$, $R_{10}$ is hydrogen, methyl, ethyl or trifluoromethyl and $R_{11}$ is an alkyl radical of the formula

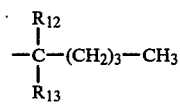

in which $R_{12}$ and $R_{13}$ have the same or a different meaning and each is hydrogen, methyl or ethyl, or $R_{11}$ is a cyclohexyl radical

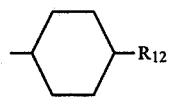

in which $R_{12}$ has the same meaning as above.
Preferred compounds of the general formula I are such wherein
$R_2$ and $R_3$ are hydrogen or methyl groups and/or
$R_4$ represents the benzoyl group and/or
$R_6$ and $R_7$ are hydrogen or methyl groups and/or
$R_8$ is methyl or ethyl and/or
$R_{10}$, $R_{12}$ and $R_{13}$ are hydrogen and/or
A is the group $-CH_2-CH_2-$.
A preferred group of compounds of the general formula I is represented by the formula

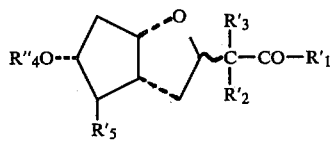

wherein
$R_1'$ is methyl or ethyl or represents the group

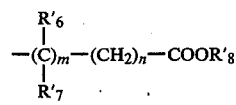

in which $R_6'$ and $R_7'$ have the same or a different meaning and each is hydrogen or methyl, m is zero or one, n is zero, one, two or three and $R_8'$ is methyl or ethyl, or
is a phenyl group optionally substituted by methyl, ethyl, trifluoromethyl or methoxy or by a group $OR_9$, in which $R_9$ has the same meaning as above, or by a fluorine, chlorine or bromine atom or by the group

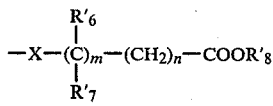

wherein X, $R_6'$, $R_7'$, $R_8'$, m and n have the same meaning as above, or is together with the radical $R_3'$ the group —$(CH_2)_r$— in which r is three, four or five;

$R_2'$ is hydrogen, methyl or the group —$(CH_2)_s$—$COOR_8'$, in which $R_8'$ and s have the same meaning as above;

$R_3'$ is hydrogen or methyl or represents together with $R_1'$ the group —$(CH_2)_r$— defined above;

$R_4''$ is a member of the group consisting of alkanoyl groups containing 1 to 5 carbon atoms, benzoyl, 4-phenylbenzoyl, trimethylsilyl, tert.butyl-dimethylsilyl and tert.butyl-diphenylsilyl, and $R_5'$ is the group —$CH_2$—$OR_4'''$ or the group

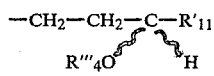

in which groups $R_4'''$ within the scope of the definition of $R_4''$ has the same or a different meaning as $R_4''$ has and in which $R_{11}'$ is a n-pentyl or a cyclohexyl group.

Preferably $R_1$ or $R_1'$, respectively, are a phenyl group substituted as defined above. A most preferred group of the compounds of general formula I corresponds to the formula

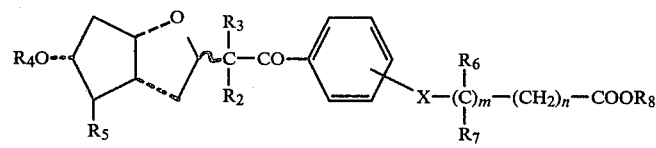

wherein $R_2$ to $R_8$, X, m and n have the same meaning as above and wherein preferably X represents a single bond while both of m and n are zero.

In this latter case the compounds especially correspond to the formula

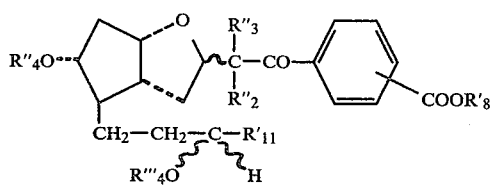

wherein $R_4''$, $R_4'''$, $R_8'$ and $R_{11}'$ have the same meaning as above and wherein $R_2''$ and $R_3''$ have the same or a different meaning and each represents hydrogen or methyl.

In the formulae given herein a dotted line (. . .) indicates that the respective substituent is attached in endo-configuration ($\alpha$-isomer) to the 2-oxabicyclo [3.3.0]octane skeleton of the formula

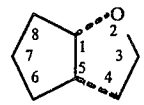

or, in case the substituent is attached to a carbon chain, the dotted line indicates that the substituent is attached in S-configuration.

Solid line (———) attachments to the basic skeleton indicate substituents in exo-configuration ($\beta$-isomer). If the substituent is attached to a carbon chain the solid line indicates R-configuration.

The use of wavy lines (∿) herein will represent that the attachment of the substituent is not defined, i.e. that the substituent may be attached in $\alpha$- or $\beta$-configuration or, if attached to a chain, in R- or S-configuration, respectively, (or in a mixture of the isomers).

The cyclopentane moiety in the compounds of formula I is attached to the tetrahydrofurane moiety of the 2-oxa-bicyclo[3.3.0]octane in cis-configuration.

The process of the invention for the preparation of the compounds of formula I comprises reacting at temperatures from about −80° C. to about +60° C. a compound of the formula

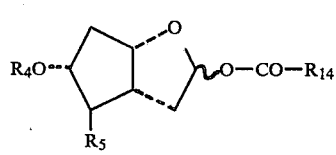

wherein $R_4$ and $R_5$ have the same meaning as in formula I and wherein $R_{14}$ represents an alkyl radical containing 1 to 4 carbon atoms, preferably the methyl group, or the phenyl radical, with a compound of the formula

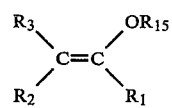

wherein $R_1$, $R_2$ and $R_3$ have the same meaning as in formula I and wherein $R_{15}$ represents a trimethylsilyl group or a lower alkanoyl group, preferably the acetyl group, in presence of one or more Lewis acids and in an inert solvent.

Suitable Lewis acids to be used in the process of the invention are preferably members of the group consisting of aluminium chloride, boron trifluoride, copper-(II)sulfate, silver perchlorate, silver tetrafluoroborate, tin(IV)chloride, titanium(IV)chloride, zinc bromide and zinc chloride. Preferably boron trifluoride (e.g. in the form of its etherate) or tin(IV)chloride, respectively, are used as Lewis acids. The Lewis acids are generally used in amounts of $10^{-3}$ moles to $10^2$ moles per mol used of the compound of formula II, but particularly equivalent amounts of the Lewis acid and of the compound of formula II are used.

Preferably the reaction is carried out at temperatures between −5° C. and +20° C.

Suitable inert solvents useful in the process of the invention include linear or cyclic ethers (e.g. diethyl ether, dimethoxyethane, dioxane or tetrahydrofuran), aliphatic or aromatic hydrocarbons, which are liquid under the reaction conditions (e.g. n-hexane, benzene or toluene) or chlorinated lower aliphatic hydrocarbons (e.g. dichloromethane, chloroform or carbon tetrachloride).

In the process of the invention mixtures of the diastereomers of the compounds of formula I are produced which can be isolated by known techniques, preferably by column chromatography. These mixtures of diastereomers may be separated e.g. by recrystallizing or by column chromatography (especially using silica gel) in the usual way. The present invention relates accordingly to the pure diastereomers and to the mixtures thereof of the compounds of formula I or more particular to the preparation of these diastereomers and their mixtures, collectively designated herein as compounds of formula I.

The process of the invention provides a new, unobvious route for the preparation of the compounds of formula I which are valuable intermediates in the preparation of important pharmacologically active prostacyclin compounds which exhibit smooth muslce dilating, antithrombotic, bronchodilating, antidermatosis and/or other therapeutically valuable bioactivity. Most of the compounds of formula I are new. So far as compounds of formula I already have been described, they were synthesized following routes difficult to perform and in most instances with small yields only. Quite to the contrary, the present invention provides a route for preparing these valuable intermediates quickly in high yields and in a very easy manner. Especially due to the easy availability and the large scope of the possible variants of the compounds of formula III, the process of the invention provides a simple, technically important route for the preparation also of numerous compounds of formula I (and accordingly for the therapeutically valuable compounds which can be made from these intermediates) which were not accessible before.

The compounds of formula I may be transformed into pharmacologically active compounds in a manner known per se e.g. (in case the group $R_5$ is different from —$CH_2$—O—$R_4'$) by splitting off the group $R_4$ (i.e. replacing this group by a hydrogen atom) and replacing the group $R_8$, if present, by a pharmaceutically acceptable cation or by a hydrogen atom or by replacing, respectively, the group(s) $R_9$ and/or $R_4'$ by hydrogen.

If $R_5$ in the compounds of formula I represents the group —$CH_2$—$OR_4'$, it is (for the preparation of pharmacologically active compounds) necessary to transform this group in a manner known per se into the group —$CH_2$—OH and (provided $R_1$ is not the methoxy, the ethoxy or the trimethylsilyloxy group) to protect the carbonyl group bearing the radical $R_1$, for instance by ketal formation with ethylene glycol or with propylene glycol. Thereafter, the hydroxy-methyl group in position 6 of the 2-oxabicyclo[3.3.0]octane derivative thus obtained is oxidized to an aldehyde group which then is transformed into the group —A—(-COH—$R_{10}$)—$R_{11}$, wherein A, $R_{10}$ and $R_{11}$ have the same meaning as above, in a manner known per se as for instance in analogy to the process described in the British patent specification No. 1,599,280. By exchanging the groups $R_4$, $R_8$ and $R_9$ with hydrogen or ($R_8$) with a cation, respectively, and deprotecting the carbonyl group bearing the group $R_1$ there are thus obtained compounds of formula

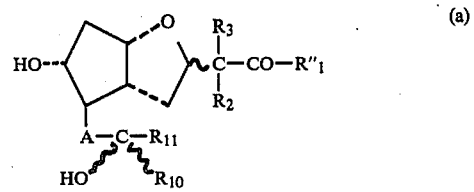

(a)

wherein $R_2$, $R_3$, $R_{10}$, $R_{11}$ and A have the same meaning as above and wherein $R_1''$ is the same as the group $R_1$ with the proviso that if $R_1''$ contains groups $R_8$ and $R_9$ these also may be hydrogen or ($R_8$) a cation, respectively.

It is possible, for instance, to reduce in a manner known per se (e.g. as described in the British patent specification No. 2,012,762) in the compounds of formula (a) the carbonyl group bearing the group $R_1''$ to give one of the groups —CHOH— or —$CH_2$— and thus to prepare pharmacologically active compounds of the formula

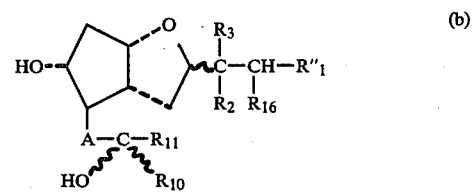

(b)

wherein $R_1''$, $R_2$, $R_3$, $R_{10}$, $R_{11}$ and A have the same meaning as above and wherein $R_{16}$ is a hydroxy group or a hydrogen atom.

Some of the starting materials for the process are already known, the others may be prepared in analogy to published methods as follows:

To prepare the compounds of general formula II lactols of the formula

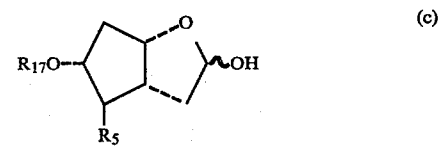

(c)

in which $R_5$ has the same meaning as above and wherein $R_{17}$ has the same meaning as $R_4$ but also may represent hydrogen are reacted e.g. with acylchlorides/pyridine in presence of solvents like ethyl acetate or with acid anhydrides/pyridine in tetrahydrofuran. Without intermediary purification the compounds of formula II formed in these reactions may be reacted with the compounds of formula III as described herein above.

The lactols of formula (c) are obtained by reduction of the corresponding lactones of the formula

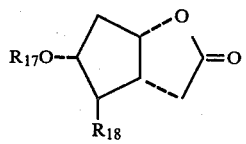

(d)

wherein R$_{17}$ has the same meaning as in formula (c) and wherein R$_{18}$ is a member of the group of compounds having the formulae

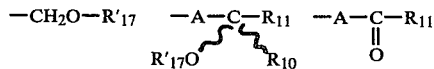

wherein A, R$_{10}$ and R$_{11}$ have the same meaning as above and wherein R$_{17}'$ within the scope of the definition of R$_{17}$ has the same or a different meaning as R$_{17}$ has. For example, the reduction may be carried out at −78° C. in a mixture of toluene and tetrahydrofuran by means of diisobutyl-aluminiumhydride [c.f. E. W. Yankee et al., J. Am. Chem. Soc. 96, 5865 (1974)].

The lactones of formula (d) may be obtained as described in the literature or in analogy to the state of the art, references for which inter alia include:

Bindra and Bindra, "Prostaglandin Synthesis", Academic Press Inc., New York, San Francisco, London 1977 or A. Mitra, "The Synthesis of Prostaglandins", John Wiley and Sons, New York, London, Sydney, Toronto 1977.

The compounds of the general formula III also may be prepared as described in literature or in an analogous manner. Reference is made to (1) Methoden der organischen Chemie (Houben Weyl) Vol. VI/1d, page 104, George Thieme Verlahg, Stuttgart 1978

(2) Methoden der organischen Chemie (Houben-Weyl) Vol. VII/2b, page 1906, Georg Thieme Verlag, Stuttgart 1976

(3) J. K. Rasmussen, Synthesis 91 (1977)

(4) R. D. Miller and D. R. McKean, Synthesis 730 (1979)

(5) J. Fleming and J. Paterson, Synthesis 736 (1979)

(6) A. Wissner, J. Org. Chem. 44, 4619 (1979)

(7) H. O. House et al., J. Org. Chem. 34, 2324 (1969).

The following non-limiting examples serve further to illustrate the invention. All temperature references are uncorrected.

The nuclear magnetic spectra were measured ($^1$H-spectra at 60 MHz, $^{13}$C-spectra at 15,08 MHz) with commercially available equipment (Bruker, WP-60). The chemical shifts are reported in ppm.

The reactions were controlled by thin layer chromatography on plates precoated with silica gel ("Kieselgel 60" of E. Merck AG, Darmstadt, Germany). In column chromatographic purifications also silica gel ("Kieselgel 60", 0.063–0.200 mm or 0.040–0.063 mm) was used.

EXAMPLE 1

3α,β-(1RS-Cyclopentane-2-one-1-yl)-6β-(3RS-acetoxy-n-octyl)-7α-benzoyloxy-2-oxabicyclo[3.3.0]octane.

700 mg of 3α,β-acetoxy-6β-(3RS-acetoxy-n-octyl)-7α-benzoyloxy-2-oxabicyclo[3.3.0]octane and 278 mg of (1-cyclopentene-l-yl-oxy)-trimethylsilane [H. O. House et al., J. Org. Chem. 34, 2324 (1969)] are dissolved in 10 ml of absolute dichloromethane. This solution is treated dropwise while stirring at 0° C. to +5° C. over a 15 minutes period with a solution of 0.18 ml of tin(IV)chloride in 10 ml of dichloromethane. The progress of the reaction is monitored by thin layer chromatography (toluene/diethylether 1:8).

The mixture is stirred at the same temperature for one further hour and then the cold solution is added dropwise, while stirring, to a saturated solution of sodium hydrogen carbonate at such a rate that the p$_H$-value is maintained at about 7.

10 ml of dichloromethane are added and after thorough shaking of the mixture, the organic layer is separated. The aqueous layer is extracted two more times with 5 ml of dichloromethane each and then the organic extracts are combined, washed twice with 3 ml of saturated sodium chloride solution each time and after drying with sodium sulfate, the solvent is distilled off in vacuo.

Thus 698 mg of the product are obtained in form of a colorless oil.

| $^1$H—NMR(CDCl$_3$) | 0.60–1.03 (m, 3H) |
| | 1.99; 2.00 (2s, 3H) |
| | 4.13–5.10 (m, 4H) |
| | 7.23–8.13 (m, 5H) |
| $^{13}$C-NMR(methanol-d$_4$) | 51.25; 52.95; 74.86; |
| | 75.11; 81.19; 83.38; |
| | 220.45. |

EXAMPLE 2

The process is the same as described in Example 1 except a solution of 0.455 ml of boron trifluoride etherate (50% BF$_3$ in diethylether) in 10 ml of dichloromethane is used instead of the tin (IV) chloride solution used in Example 1. Thus 682 mg of the product are obtained in form of a colorless oil, the spectroscopic data of which were identical with those of the product obtained in Example 1.

The hemiacetal acylal used as starting material in Examples 1 and 2 may be obtained as follows:

(a) A stirred solution of 5 g of 3-oxo-6β-(3-oxo-n-octyl)-7α-benzoyloxy-2-oxabicyclo[3.3.0]octane [W. Skuballa et al., J.Med.Chem. 21, 443 (1978)] in 100 ml of absolute tetrahydrofurane is reacted under an atmosphere of dry nitrogen at −78° C. dropwise with 100 ml of a solution of diisobutylaluminiumhydride (about 0.6 moles/l) in toluene. The reaction mixture is thereafter stirred for further 30 minutes at −78° C. The progress of the reaction is monitored by thin layer chromatography (toluene/acetone 1:1).

After the end of the reaction the mixture is treated dropwise, while chilling, with 100 ml of saturated ammonium chloride solution. Thereafter the mixture is slowly heated to room temperature, filtered by using about 30 g of filter aid (pretreated with ethyl acetate) and the filter aid containing the precipitate is washed four times with ethyl acetate. The combined filtrates form two layers which are separated. The organic layer is washed twice with 30 ml of saturated sodium chloride solution, dried over sodium sulfate and evaporated in vacuo to give 4.6 g of an almost colorless oil. This is purified by column chromatography using toluene/acetone (1:1) to give 4.5 g of the product in form of a colorless oil.

| $^1$H—NMR(CDCl$_3$) | 0.70–1.17 (m, 3H) |

-continued

| | |
|---|---|
| | 3.30–3.80 (m, 1H) |
| | 4.56–5.26 (m, 2H) |
| | 5.40–5.80 (m, 1H) |
| | 7.07–8.17 (m, 5H) |

(b) 3α,β-Acetoxy-6β-(3RS-acetoxy-n-octyl)-7α-benzoyloxy-2-oxa-bicyclo[3.3.0]octane.

A solution of 1.32 g of the product obtained in step (a) in a mixture of 3.3 ml of absolute tetrahydrofuran and 3.3 ml of absolute pyridine is chilled with ice and then slowly reacted dropwise with 3.3 ml of acetic anhydride. After stirring for one hour in the ice bath and thereafter for about 15 hours at room temperature (the progress of the reaction is monitored by thin layer chromatography using the solvent system dichloromethane:acetone=4:1) the volatile constituents of the mixture are distilled off at about 10 to 12 Torr and finally in a high vacuum at about 40° to 45° C. bath temperature using a rotating evaporator.

Thus the product is obtained in a yield of 1.56 g in form of a colorless oil.

| $^1$H—NMR(CDCl$_3$) | |
|---|---|
| | 0.60–1.06 (m, 3H) |
| | 2.03–2.06 (2s, 6H) |
| | 4.57–5.20 (m, 3H) |
| | 6.17–6.47 (m, 1H) |
| | 7.20–8.03 (m, 5H) |

EXAMPLE 3

3α,β-(1RS-Cyclopentane-2-one-1-yl)-6β-acetoxymethyl-7α-benzoyloxy-2-oxabicyclo[3.3.0]octane.

A solution of 10 g of 3α,β-acetoxy-6β-acetoxymethyl-7α-benzoyloxy-2-oxa-bicyclo[3.3.0]octane and 4.3 g of (1-cyclopentene-1-yl-oxy)-trimethylsilane in 200 ml of absolute dichloromethane is reacted at 0° to 5° C., while stirring, dropwise with a solution of 0.83 ml of boron trifluoride etherate (50% BF$_3$ in diethylether) in 20 ml of dichloromethane. The progress of the reaction is monitored by thin layer chromatography (toluene/diethylether 1:8). After an additional reaction period of 30 minutes at the same temperature the cold solution is added dropwise to a stirred saturated solution of sodium hydrogen carbonate at such a rate that the p$_H$-value is maintained at about 7. After adding 500 ml of dichloromethane and thoroughly shaking the mixture, the organic layer is separated. The aqueous layer is extracted twice with 50 ml of dichloromethane each time and then the organic layers are combined, washed twice with 20 ml of saturated sodium chloride solution each time, dried over sodium sulfate and evaporated to give 10.5 g of a light yellow oil. On column chromatography using toluene/diethylether (1:8) this gives the product in a yield of 9.4 g and in form of a colorless oil.

| $^1$H—NMR(CDCl$_3$) | 2.00 (m,3H) |
|---|---|
| | 3.97–4.20 (d, 2H) |
| | 4.34–5.30 (m, 3H) |
| | 7.33–8.20 (m, 5H) |
| $^{13}$C—NMR(CDCl$_3$) | 49.27; 52.05; 76.58; |
| | 77.71; 81.83; 81.96; |
| | 220.00. |

EXAMPLE 4

The procedure is the same as in Example 3 except that a solution of 3.3 ml of tin (IV) chloride in 20 ml of dichloromethane is used instead of the solution of boron trifluoride etherate. 9.0 g of the same product as obtained in Example 3, shown by the identity of the spectroscopic data, are thus obtained.

The hemiacetal acylal used as starting material in Examples 3 and 4 may be obtained as follows:

(c) 3α,β-Hydroxy-6β-hydroxymethyl-7α-benzoyloxy-2-oxa-bicyclo[3.3.0]octane.

A stirred solution of 5 g of 3-oxo-6β-hydroxymethyl-7α-benzoyloxy-2-oxa-bicyclo[3.3.0]octane in 200 ml of absolute tetrahydrofuran is treated under an atmosphere of dry nitrogen at −78° C. dropwise with 75 ml of a solution of diisobutylaluminiumhydride (about 1.2 moles/l) in toluene. The further procedure is the same as described in (a) under Example 2 whereby 4.9 g of the product are obtained in form of an almost colorless oil which can be used in the next step without further purification. It may, however, be purified by column chromatography using dichloromethane/acetone (4:1) whereby it is obtained in form of a colorless oil.

| $^1$H—NMR(CDCl$_3$) | 3.16–3.28 (d,2H) |
|---|---|
| | 4.47–5.80 (m, 3H) |
| | 7.23–8.17 (m, 5H) |

(d) 3α,β-Acetoxy-6β-acetoxymethyl-7α-benzoyloxy-2-oxabicyclo[3.3.0]octane.

To a solution of 1 g of the product obtained in step (c) in 3 ml of absolute tetrahydrofuran 4 ml of absolute pyridine are added. The mixture is chilled in an ice bath, then reacted dropwise with 4 ml of acetic anhydride, followed by storage for one hour in the ice bath and finally for 15 hours at room temperature, whereafter it is worked up in the same manner as described in Example 2, section (b). 1.2 g of the title compound are thus obtained in the form of a colorless oil.

| $^1$H—NMR(CDCl$_3$) | 2.00; 2.05 (2s, 6H) |
|---|---|
| | 3.97–4.20 (d, 2H) |
| | 4.53–5.40 (m, 2H) |
| | 6.17–6.47 (m, 1H) |
| | 7.20–8.10 (m, 5H) |
| $^{13}$C—NMR(CDCl$_3$) | 64.45; 84.10; 100.35; |
| | 166.10; 170.30; 170.86. |

EXAMPLE 5

3α,β-(Propane-2-one-1-yl)-6β-(3RS-acetoxy-n-octyl)-7α-benzoyloxy-2-oxabicyclo[3.3.0]octane.

To a stirred solution of 100 mg of 3α,β-acetoxy-6β-(3RS-acetoxy-n-octyl)-7α-benzoyloxy-2-oxabicyclo[3.3.0]octane and 25 mg of α-methylvinyl acetate in 3 ml of absolute dichloromethane, chilled with ice water, is slowly added dropwise a solution of 0.0255 ml of tin(IV) chloride in 2 ml of dichloromethane. The cold mixture is stirred for about one hour, during which period the progress of the reaction is monitored by thin layer chromatography (diisopropylether/diethylether 3:2).

Thereafter the cold solution is added dropwise, while stirring, to 20 ml of a saturated aqueous solution of sodium hydrogen carbonate. The mixture is then worked up in the manner described in Example 1 to give 90 mg of a yellowish oil which on column chromatography with diisopropylether/diethylether (3:2)

yields 60 mg of the title compound in form of a colorless oil.

| $^1$H—NMR(CDCl$_3$) | 0.63–1.10 (m, 3H) |
| --- | --- |
|  | 1.97; 2.00 (2s, 3H) |
|  | 2.16 (s, 3H) |
|  | 4.23–5.07 (m, 4H) |
|  | 7.20–8.10 (m, 5H) |

EXAMPLE 6

The procedure is the same as described in Example 5, except that a solution of 0.0065 ml of boron trifluoride etherate (50% BF$_3$ in diethylether) in 2 ml of dichloromethane is used instead of the tin (IV) chloride solution. Thereby 65 mg of a colorless oil are obtained showing spectroscopic data identical with those of the product obtained in Example 5.

EXAMPLE 7

3α,β-(Propane-2-one-1-yl)-6β-acetoxymethyl-7α-benzoyloxy-2-oxabicyclo[3.3.0]octane.

100 mg of 3α,β-acetoxy-6β-acetoxymethyl-7α-benzoyloxy-2-oxabicyclo[3.3.0]octane and 30 mg of α-methylvinyl acetate dissolved in 3 ml of absolute dichloromethane, are reacted by adding a solution of 0.0083 ml of boron trifluoride etherate (50% BF$_3$ in diethylether) in 2 ml of dichloromethane in the manner described in Example 5. Working up in the described manner yields 95 mg of the title compound in form of a colorless oil.

| $^1$H—NMR(CDCl$_3$) | 1.97; 2.00 (2s, 3H) |
| --- | --- |
|  | 2.16 (s, 3H) |
|  | 3.83–5.40 (m, 5H) |
|  | 7.20–8.20 (m, 5H) |

EXAMPLE 8

3α,β-[2-(2'-Methoxycarbonylphenyl)-ethane-2-one-1-yl]-6β-(3RS-acetoxy-n-octyl)-7α-benzoyloxy-2-oxabicyclo[3.3.0]octane.

A solution of 1 g of 3α,β-acetoxy-6β-(3RS-acetoxy-n-octyl)-7α-benzoyloxy-2-oxabicyclo[3.3.0]octane and 0.6 g of 1-trimethylsilyloxy-1-(2'methoxycarbonylphenyl)-ethylene in 20 ml of absolute dichloromethane at 0° to +5° C. is slowly treated dropwise with a solution of 0.246 ml of tin(IV)chloride in 10 ml of dichloromethane, while stirring. The progress of the reaction is monitored by thin layer chromatography (diisopropylether/diethylether 3:2) and after an additional hour the still cold reaction mixture is added to a stirred saturated solution of sodium hydrogen carbonate in such a manner that the p$_H$ value is maintained at about 7. After addition of 20 ml of dichloromethane the mixture is shaken. The layers are separated and the aqueous layer is extracted two more times with 10 ml of dichloromethane each time. The combined organic extracts are washed twice with saturated sodium chloride solution, dried over sodium sulfate and finally evaporated. The residue is purified by column chromatography with diisopropylether/diethylether (3:2) to give 1.1 g of the title compound in form of a colorless oil.

| $^1$H—NMR(CDCl$_3$) | 0.57–1.06 (m,3H) |
| --- | --- |
|  | 2.00 (s,3H) |

| | -continued |
| --- | --- |
|  | 2.93–3.27 (m,2H) |
|  | 3.77; 3.88 (2s,3H) |
|  | 4.33–5.08 (m,4H) |
|  | 7.23–8.09 (m,5H) |
| $^{13}$C—NMR(acetone-d$_6$) | 48.51; 74.33; 82.16; |
|  | 168.32; 171.38; 206.80. |

The silated compound used as starting material in this Example is obtained as follows:

A solution of 17.8 g of methyl 2-acetylbenzoate [M. S. Newman et al., J.Org.Chem. 27, 863 (1962)] and 16.5 ml of triethylamine (freshly distilled over solid potassium hydroxide) in 80 ml of toluene (distilled over sodium hydride) at 20° to 25° C. is reacted dropwise with a solution of 18.4 ml of trimethylsilyl trifluoromethanesulfonate in 10 ml of toluene. The mixture is stirred for three hours and then allowed to stand whereby it forms two layers. The (upper) toluene layer is separated and evaporated. The remaining oil is distilled in vacuo to give 10.2 g of the desired product, boiling at 11 Torr and 125° to 127° C.

| $^1$H—NMR(CDCl$_3$) | 3.80 (s, 3H) |
| --- | --- |
|  | 4.30–4.57 (2d, 2H) |
|  | 7.10–7.80 (m, 4H) |

EXAMPLE 9

3α,β-[2-(2'-methoxycarbonylphenyl)ethane-2-one-1-yl]-6β-acetoxymethyl-7α-benzoyloxy-2-oxabicyclo[3.3.0]octane.

A solution of 100 mg of 3α,β-acetoxy-6β-acetoxymethyl-7α-benzoyloxy-2-oxabicyclo[3.3.0]octane and 70 mg of 1-trimethylsilyloxy-1-(2'-methoxycarbonylphenyl)-ethylene in 3 ml of absolute dichloromethane is treated, while stirring, at 0° C. to 5° C. dropwise with a solution of 0.0033 ml of tin(IV)chloride in 3 ml of dichloromethane. The progress of the reaction is monitored by thin layer chromatography (diisopropylether/diethylether 3:1). After stirring for 15 minutes the cold reaction mixture is worked up in the manner described in Example 5. Column chromatography of the crude product with diisopropylether/diethylether 3:2 yields 50 mg of the title compound in form of a colorless oil.

| $^1$H—NMR(CDCl$_3$) | 2.00 (s, 3H) |
| --- | --- |
|  | 2.91–3.23 (m, 2H) |
|  | 3.61–5.40 (m, 8H) |
|  | 7.03–8.17 (m, 4H) |

EXAMPLE 10

The procedure is the same as described in Example 9, except that a solution of 0.0083 ml of boron trifluoride etherate (50% BF$_3$ in diethylether) in 3 ml of dichloromethane is used instead of the tin (IV) chloride. After purification by column chromatography 45 mg of the same product as in Example 9 are obtained proven by identity of the spectroscopic data.

EXAMPLE 11

3α,β-(1RS-Propane-2-one-1-ethoxycarbonyl-1-yl)-6β-(3RS-acetoxy-n-octyl)-7α-benzoyloxy-2-oxabicyclo[3.3.0]octane.

100 mg of 3α,β-acetoxy-6β-(3RS-acetoxy-n-octyl)-7α-benzoyloxy-2-oxabicyclo[3.3.0]octane and 44 mg of ethyl 3-trimethylsilyloxycrotonate [W. Kantlehner et al., Chem.Ber. 105, 2264 (1972)] are dissolved in 3 ml of dichloromethane. This solution is chilled to −10° C. and at that temperature treated slowly dropwise with a solution of 0.0246 ml of tin((IV)chloride in 3 ml of dichloromethane, while stirring. The progress of the reaction is monitored by thin layer chromatography (diethylether/hexane 2:1). After stirring for about 30 minutes, while cooling, the mixture is worked up in the manner described in Example 5 to give 110 mg of the product in form of a slightly yellowish oil.

| $^1$H—NMR(CDCl$_3$): | 0.60–1.00 (m,3H) |
|---|---|
| | 2.00; 2.03 (2s,3H) |
| | 2.13–2.30 (m,3H) |
| | 3.33–3.70 (m,1H) |
| | 3.90–5.27 (m,6H) |
| | 7.23–8.13 (m,5H) |
| $^{13}$C—NMR(CDCl$_3$): | 61.41; 61.53; 64.57; |
| | 79.24; 79.85; 201.64. |

EXAMPLE 12

3α,β-(1RS-Propane-2-one-1-ethoxycarbonyl-1-yl)-6β-acetoxymethyl-7α-benzoyloxy-2-oxabicyclo[3.3.0]octane.

A stirred solution of 200 mg of 3α,β-acetoxy-6β-acetoxymethyl-7α-benzoyloxy-2-oxabicyclo[3.3.0]octane and 112 mg of ethyl 3-trimethylsilyloxycrotonate in 5 ml of absolute dichloromethane is chilled in an ice-water bath and treated dropwise with a solution of 0.066 ml tin(IV)chloride in 4 ml of dichloromethane. The progress of the reaction is monitored by thin layer chromatography (diisopropylether/diethylether 3:1). After about 15 minutes the reaction mixture is worked up in the manner described in Example 5. The crude product is purified by column chromatography (diisopropylether/diethylether 3:2) to yield 122 mg of the product in form of a colorless oil.

| $^1$H—NMR(CDCl$_3$): | 1.03–1.26 (m,3H) |
|---|---|
| | 2.00 (s,3H) |
| | 2.13–2.30 (m,3H) |
| | 3.33–3.70 (m,1H) |
| | 3.90–5.27 (m,7H) |
| | 7.17–8.03 (m,5H) |

EXAMPLE 13

3α,β-(1RS-Methoxycarbonyl-1-benzoyl-propyl-1)-6β-(3RS-acetoxy-n-octyl)-7α-benzoyloxy-2-oxabicyclo[3.3.0]octane.

A solution of 461 mg of 3α,β-acetoxy-6β-(3RS-acetoxy-n-octyl)-7α-benzoyloxy-2-oxabicyclo[3.3.0]octane and 306 mg of 5-trimethylsilyloxy-5-phenyl-4-pentenoic acid methyl ester (R. D. Miller et al., Synthesis 1979, 730) in 5 ml of absolute dichloromethane is treated, while cooling with ice and stirring, dropwise with a solution of 0.12 ml of tin(IV)chloride in 5 ml of absolute dichloromethane. The progress of the reaction is controlled by thin layer chromatography (diethylether/diisopropylether/hexane 1:1:1). After 60 minutes the reaction mixture is added dropwise to 30 ml of saturated sodium hydrogen carbonate solution chilled with ice in such a manner that the p$_H$ value remains at about 7. The organic layer is separated and the aqueous layer is extracted three times with small amounts of dichloromethane. The combined organic extracts are washed with 20 ml of saturated sodium chloride solution, dried over sodium sulfate and evaporated in a rotating evaporator in a vacuum at bath temperatures below 30° C. The crude product (585 mg) is purified by column chromatography with diethylether/diisopropylether/hexane (1:1:1) to give 523.6 mg of the product in form of a colorless oil.

| $^1$H—NMR(CDCl$_3$): | 0.6–1.0 (m,3H) |
|---|---|
| | 3.57 (s,3H) |
| | 3.35–3.87 (m,1H) |
| | 4.1–5.05 (m,4H) |
| | 7.2–7.63 (m,6H) |
| | 7.7–8.12 (m,4H) |

EXAMPLE 14

3α,β-(1RS-1-Ethylpentane-2-one-1-yl)-6β-(3RS-acetoxy-n-octyl)-7α-benzoyloxy-2-oxabicyclo[3.3.0]octane.

A solution of 400 mg of 3α,β-acetoxy-6β-(3RS-acetoxy-n-octyl)-7α-benzoyloxy-2-oxabicyclo[3.3.0]octane and of 162 mg of 4-trimethylsilyloxy-hept-3-ene in 5 ml of absolute dichloromethane is treated dropwise with a solution of 0,1 ml of tin(IV)chloride in 1 ml of absolute dichloromethane. The progress of the reaction is monitored by thin layer chromatography (diisopropylether/hexane 4:1). After 30 minutes the reaction mixture is worked up in the manner described in Example 13 to give 391.4 mg crude product. This is purified by column chromatography (diisopropylether/hexane 4:1) to yield 313.6 mg of the title product in form of a colorless oil.

| $^1$H—NMR(CDCl$_3$): | 0.6–1.03 (m,9H) |
|---|---|
| | 2.0 (s,3H) |
| | 3.9–5.07 (m,4H) |
| | 7.23–7.6 (m,3H) |
| | 7.7–8.15 (m,2H) |
| $^{13}$C—NMR (acetonitrile-d$_3$): | 7474; 74.98; 79.12; |
| | 80.4; 81.01; 82.53; |
| | 82.96; 167.07; 172.12; |
| | 214.42; 214.85. |

The 4-trimethylsilyloxy-hept-3-ene is prepared by reacting 4-heptanone with trimethyliodosilane in presence of hexamethyldisilazane in pentane using the general method described by R. D. Miller et al., Synthesis 1979, 730. From 11.4 g of 4-heptanone 14.77 of 4-trimethylsilyloxy-hept-3-ene boiling at 0.3 Torr and 29° C. were obtained.

| $^1$H—NMR(CDCl$_3$): | 0.24 (s,9H) |
|---|---|
| | 0.7–1.1 (m,6H) |
| | 4.24–4.75 (m,1H) |

EXAMPLE 15

3α,β-(4-Ethoxycarbonyl-2-oxo-3,3-dimethyl-butyl-1)-6β-(3RS-acetoxy-n-octyl)-7α-benzoyloxy-2-oxabicyclo[3.3.0]octane.

(a) 6.18 g of ethyl 3,3-dimethyl-levulinate were reacted using the conditions of the general method described by Miller et al., Synthesis 1979, 730, to give after distillation 7 g of 1-ethoxycarbonyl-2,2-dimethyl-3-trimethylsilyloxy-but-3-ene boiling at 20 Torr and 106° to 109° C., contaminated by small amounts of starting material. The pure compound was obtained by column chromatography (diethylether/hexane 1:1) of the distillate.

| $^1$H—NMR(CDCl$_3$): | 1.24 (s,9H) |
| --- | --- |
| | 2.25–2.47 (d,2H) |
| | 3.85–4.27 (q + 2d,4H) |

(b) To a stirred solution of 172.1 mg of 3α,β-acetoxy-6β-(3RS-acetoxy-n-octyl)-7α-benzoyloxy-2-oxabicyclo[3.3.0]octane and 93.1 mg of 1-ethoxycarbonyl-2,2-dimethyl-3-trimethylsilyloxy-but-3-ene in 3 ml of absolute toluene chilled with ice there is added one drop of boron trifluoride etherate solution (50% BF$_3$ in diethylether). The mixture is stirred for one hour in the ice bath and for one further hour at room temperature during which periods the progress of the reaction is monitored by thin layer chromatography (diethylether/hexane 1:1). Then it is worked up in the manner described in Example 13. Column chromatography with diethylether/hexane (1:1) yields 46.6 mg of the title compound in form of a colorless oil and from other fractions further 16.9 mg of material containing small amounts of impurities.

EXAMPLE 16

To a stirred solution of 540.5 mg of 3α,β-acetoxy-6β-(3RS-acetoxy-n-octyl)-7α-benzoyloxy-2-oxabicyclo[3.3.0]octane and 286.8 mg of 1-ethoxycarbonyl-2,2-dimethyl-3-trimethylsilyloxy-but-3-ene in 10 ml of toluene chilled with ice there is added a solution of 0.138 ml of tin(IV) chloride in 10 ml of absolute toluene. The further procedure is the same as described in Example 15b. Thus 347.7 mg of the same product as prepared in Example 15b are obtained, spectroscopic data of which are:

| $^1$H—NMR(CDCl$_3$): | 0.6–1.01 (m,3H) |
| --- | --- |
| | 1.24 (s) |
| | 2.0; 2.01 (2s,3H) |
| | 3.84–5.15 (m + q,6H) |
| | 7.23–7.55 (m,3H) |
| | 7.8–8.1 (m,2H) |

EXAMPLE 17

3α,β-(1RS-2-Ethoxycarbonyl-1-acetyl-ethyl-1)-6β-(3RS-acetoxy-n-octyl)-7α-benzoyloxy-2-oxabicyclo[3.3.0]octane.

A solution of 558.6 mg of 3α,β-acetoxy-6β-(3RS-acetoxy-n-octyl)-7α-benzoyloxy-2-oxabicyclo[3.3.0]octane and 524.8 mg of 1-ethoxycarbonyl-3-trimethylsilyloxy-but-2-ene in 10 ml of absolute toluene is treated, while chilling with ice and stirring, with a solution of 0.14 ml of tin(IV)chloride in 10 ml of absolute toluene. The progress of the reaction is monitored by thin layer chromatography (diethylether/hexane 1:1). The mixture is stirred for 2 hours and then it is worked up in the manner described in Example 13 to give 655.8 mg of crude product. This on column chromatography yields 186.5 mg of the title compound in form of a colorless oil and from further fractions 63.9 mg of product containing small amounts of impurities.

| $^1$H—NMR(CDCl$_3$): | 0.6–1.0 (m,3H) |
| --- | --- |
| | 2.0; 2.01 (2s,3H) |
| | 2.27; 2.29 (2s,3H) |
| | 3.42–3.88 (m,1H) |
| | 3.75–5.13 (m + q,6H) |
| | 7.2–7.55 (m,3H) |
| | 7.75–8.1 (m,2H) |

The 1-ethoxycarbonyl-3-trimethylsilyloxy-but-2-ene used as one of the starting materials is obtained from ethyl levulinate by reacting it with lithium diisopropylamide and trimethylchlorosilane in absolute toluene following the preparative method described by Fleming et al., Synthesis 1979, 736. It boiled at 18 Torr and 100° to 105° C.

| $^1$H—NMR(CDCl$_3$): | 0.22 (s,9H) |
| --- | --- |
| | 1.05–1.45 (t,3H) |
| | 1.79 (d,3H) |
| | 2.90–3.12 (d,2H) |
| | 3.87–4.33 (q,2H) |
| | 4.44–4.77 (t,1H) |

The foregoing description has been set forth merely for the purposes of illustration and is not intended to be limiting. Since modifications of the disclosed embodiments incorporating the spirit and substance of the invention may occur to persons skilled in the art, the scope of the invention should be limited solely with respect to the appended claims and equivalents.

What we claim is:

1. Process for the preparation of 2-oxa-bicyclo[3.3.0]octane derivatives having the formula

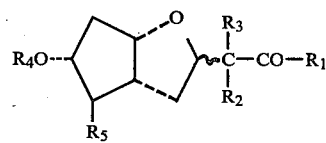

wherein
R$_1$ is an alkyl radical containing 1 to 5 carbon atoms, or
represents the group

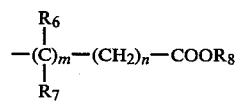

in which R$_6$ and R$_7$ have the same or a different meaning and each is a hydrogen atom or an alkyl radical containing 1 to 4 carbon atoms or R$_6$ and R$_7$ together represent the group —(CH$_2$)$_p$— wherein p is four, five or six, and m is zero or one, n is zero, one, two or three and R$_8$ is an easily removable ester residue, or is the group —(CH$_2$)$_q$—OR$_9$, in which q is one, two or three and R$_9$ is a member of the group consisting of acetyl, benzoyl, trimethylsilyl, tert.butyl-dimethylsilyl and tert.butyl-diphenylsilyl, or is an unsubstituted phenyl group or a phenyl group substituted by methyl, ethyl, trifluoromethyl or methoxy or by a group OR$_9$ in which R$_9$ has the same meaning as above, or by fluorine, chlorine or bromine or by the group

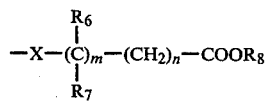

in which X is a single bond or an oxygen atom and in which $R_6$, $R_7$, $R_8$, m and n have the same meaning as above, or represents together with the radical $R_3$ the group —$(CH_2)_r$— in which r is three, four or five;

$R_2$ is a hydrogen atom, an alkyl radical containing 1 to 4 carbon atoms or the group —$(CH_2)_s$—$COOR_8$, in which $R_8$ has the same meaning as above and s is zero, one or two;

$R_3$ is a hydrogen atom, an alkyl radical containing 1 to 4 carbon atoms or together with $R_1$ is the group —$(CH_2)_r$ defined above;

$R_4$ is an acyl radical, a tri-lower-alkylsilyl group, a tert.butyl-diphenylsilyl group or a triphenylsilyl group and $R_5$ is the group —$CH_2$—$OR_4'$ or the group

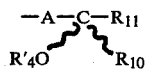

in which groups $R_4'$ within the scope of the definition of $R_4$ has the same or a different meaning as $R_4$ has and in which A represents a member of the group consisting of the groups —$CH_2$—$CH_2$—, (trans)—$CH=CH$— and —$C\equiv C$—, $R_{10}$ is hydrogen, methyl, ethyl or trifluoromethyl and $R_{11}$ is an alkyl radical of the formula

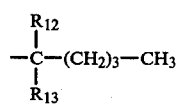

in which $R_{12}$ and $R_{13}$ have the same or a different meaning and each is hydrogen, methyl or ethyl, or $R_{11}$ is a cyclohexyl radical

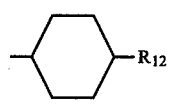

in which $R_{12}$ has the same meaning as above, comprising reacting at temperatures from about $-80°$ C. to about $+60°$ C. a compound of the formula

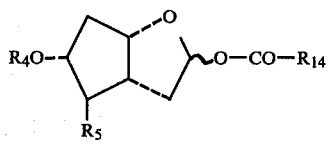

II wherein $R_4$ and $R_5$ have the same meaning as in formula I and wherein $R_{14}$ represents an alkyl radical containing 1 to 4 carbon atoms or the phenyl group with a compound of the formula

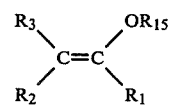

III wherein $R_1$, $R_2$ and $R_3$ have the same meaning as in formula I and wherein $R_{15}$ represents a trimethylsilyl group or a lower alkanoyl group, in presence of one or more Lewis acids and in an inert solvent.

2. Process according to claim 1 for the preparation of 2-oxa-bicyclo[3.3.0]octane derivatives having the formula

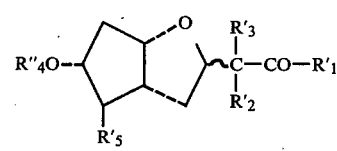

Ia wherein $R_1'$ is a methyl of an ethyl group, or represents the group

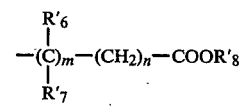

in which $R_6'$ and $R_7'$ have the same or a different meaning and each is a hydrogen atom or a methyl group, m is zero or one, n is zero, one, two or three and $R_8'$ is a methyl or an ethyl group, or in an unsubstituted phenyl group or a phenyl group substituted by methyl, ethyl, trifluoromethyl or methoxy or by a group $OR_9$ in which $R_9$ is a member of the group consisting of acetyl, benzoyl, trimethylsilyl, tert.butyl-dimethylsilyl and tert.butyl-diphenylsilyl, or by a fluorine, chlorine or bromine atom or by the group

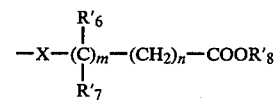

in which X is a single bond or an oxygen atom and in which $R_6'$, $R_7'$, $R_8'$, m and n have the same meaning as above, or represents together with the radical $R_3'$ the group —$(CH_2)_r$— in which r is three, four or five;

$R_2'$ is a hydrogen atom, a methyl group or the group —$(CH_2)_2$—$COOR_8'$ in which $R_8'$ has the same meaning as above and s is zero, one or two;

$R_3'$ is hydrogen or methyl or represents together with $R_1'$ group —$(CH_2)_4$— defined above;

$R_4''$ is a member of the group consisting of alkanoyl radicals containing 1 to 5 carbon atoms, benzoyl, 4-phenylbenzoyl, trimethylsilyl, tert.butyldimethylsilyl and tert.butyl-diphenylsilyl; and $R_5'$ is the group —$CH_2$—$O$—$R_4'''$ or the group

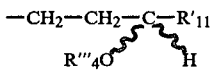

in which groups $R_4'''$ within the scope of the definition of $R_4''$ has the same or a different meaning as $R_4''$ has and in which $R_{11}'$ is a n-pentyl or a cyclohexyl group
comprising reacting at temperatures from about $-80°$ C. to about $+60°$ C. a compound of the formula

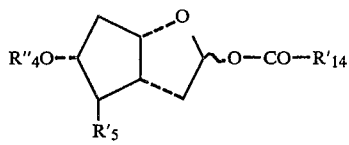

IIa wherein $R_4''$ and $R_5'$ have the same meaning as above and wherein $R_{14}'$ represents an alkyl radical containing 1 to 4 carbon atoms, or the phenyl radical, with a compound of the formula

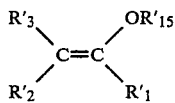

IIIa wherein $R_1'$, $R_2'$ and $R_3'$ have the same meaning as above and wherein $R_{15}'$ represents a trimethylsilyl group or an acetyl radical in presence of one or more Lewis acids and in an inert solvent.

3. Process according to claim 1 for the preparation of 2-oxa-bicyclo[3.3.0]octane derivatives having the formula

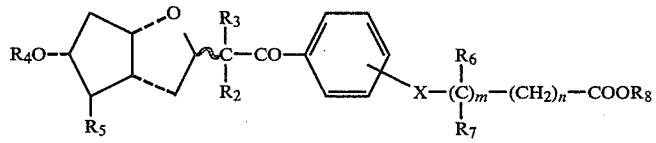

Ib wherein $R_2$ to $R_8$, X, m and n have the same meaning as defined in claim 1, comprising reacting at temperatures from about $-80°$ C. to about $+60°$ C. a compound of formula II of claim 1 with a compound of the formula

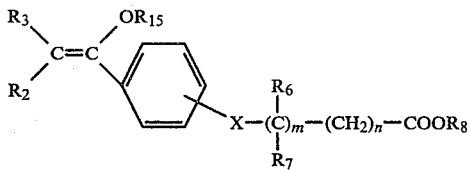

IIIb wherein $R_2$, $R_3$, $R_6$, $R_7$, $R_8$, $R_{15}$, X, m and n have the same meaning as defined in claim 1, in presence of one or more Lewis acids and in an inert solvent.

4. Process according to claim 2 for the preparation of 2-oxa-bicyclo[3.3.0]octane derivatives having the formula

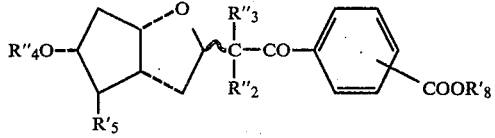

wherein $R_4''$, $R_5'$ and $R_8'$ have the same meaning as defined in claim 2 and wherein $R_2''$ and $R_3''$ have the same or a different meaning and each is a hydrogen atom or a methyl group
comprising reacting at temperatures from about $-80°$ C. to about $+60°$ C. a compound of formula IIa of claim 2 with a compound of the formula

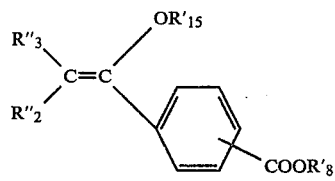

IIIc wherein $R_2''$ and $R_3''$ have the same meaning as above and $R_8'$ and $R_{15}'$ have the same meaning as defined in claim 2 in presence of one or more Lewis acids and in an inert solvent.

5. Process according to any one of claims 1 to 4 wherein the Lewis acids used in the reaction are selected from the group consisting of aluminium chloride, boron trifluoride, copper(II)sulfate, silver perchlorate, silver tetrafluoroborate, tin(IV)chloride, titanium(IV)chloride, zinc bromide and zinc chloride.

6. Process according to any one of claims 1 to 4 wherein the Lewis acid used in the reaction is boron trifluoride or tin(IV)chloride.

7. Process according to any one of claims 1 to 4 wherein the Lewis acids are used in amounts of $10^{-3}$ moles to $10^2$ moles, per mole used of the compound of formula II or IIa, respectively.

8. Process according to any one of claims 1 to 4 wherein the reaction temperature is from about $-5°$ C. to about $+20°$ C. and wherein the inert solvent is a chlorinated lower aliphatic hydrocarbon.

9. Process according to claim 1 wherein $R_1$ represents a radical selected from the group consisting of methyl and ethyl.

10. Process according to claim 2 wherein $R_4''$ represents an acetyl radical.

11. Process according to claim 2 wherein $R_{14}'$ represents a methyl radical.

12. Process according to claim 7 wherein the Lewis Acids are used in equimolar amounts per mole of the compound corresponding to formula II.

13. Process according to claim 8 wherein said inert solvent is dichloromethane.

14. A compound of the formula:

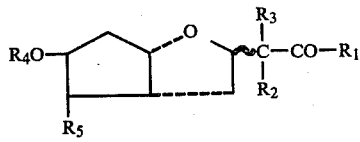

wherein $R_3$ is hydrogen or alkyl of 1-4 carbons;

$R_2$ is $COOR_8$ wherein $R_8$ is methyl or ethyl group; $R_4$ is alkanoyl containing 1-5 carbon atoms, benzoyl; 4-phenyl benzoyl, tri-lower alkyl silyl group, a tert-butyldiphenylsilyl group or a triphenylsilyl group;

$R_1$ is an alkyl radical containing 1-5 carbon atoms, or represents together with the radical $R_3$ the group $-(CH_2)_r-$ in wich r is three, four, or five or is an unsubstituted phenyl group or a phenyl group substituted by methyl, ethyl, trifluoromethyl, fluorine, chlorine or bromine;

$R_5$ is the group

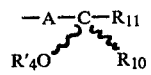

in which group $R_4'$ within the scope of the definition of $R_4$ has the same or a different meaning as $R_4$ has and in which A represents a member selected from $-CH_2-CH_2-$, (trans)-$CH=CH-$ and $-C\equiv C-$, $R_{10}$ is hydrogen, methyl, ethyl, or trifluoromethyl and $R_{11}$ is an alkyl radical of the formula

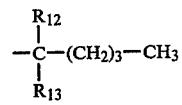

in which $R_{12}$ and $R_{13}$ have the same or a different meaning and each is hydrogen, methyl, or ethyl or $R_{11}$ is a cyclohexyl radical

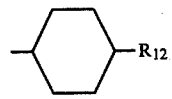

in which $R_{12}$ has the same meaning as above, in the form of their pure isomeric forms or mixtures thereof.

* * * * *